United States Patent [19]

Tóth et al.

[11] 4,119,633

[45] * Oct. 10, 1978

[54] 2-PHENOXY AND 2-PHENYLTHIO AND 2-PHENYLAMINO-ALKYL-2-OXAZOLINES

[75] Inventors: István Tibor Tóth; Pál Bite; György Magyar; Eszter Diszler; József Borsy; Andrea Maderspach; István Polgári; Sándor Elek; István Elekes, all of Budapest, Hungary

[73] Assignee: Chinoin Gyógyszer és Vegyészeti Termékek Gyára RT., Budapest, Hungary

[*] Notice: The portion of the term of this patent subsequent to Sep. 7, 1993, has been disclaimed.

[21] Appl. No.: 715,051

[22] Filed: Aug. 17, 1976

Related U.S. Application Data

[63] Continuation-in-part of Ser. No. 406,784, Oct. 16, 1973, Pat. No. 3,979,405.

[30] Foreign Application Priority Data

Oct. 20, 1972 [HU] Hungary ............... GO 1222

[51] Int. Cl.$^2$ ............................................. C07D 263/14
[52] U.S. Cl. ................................. 260/307 F; 424/272
[58] Field of Search ................... 260/307 F; 424/272

[56] References Cited

U.S. PATENT DOCUMENTS

| | | | |
|---|---|---|---|
| 3,778,445 | 12/1973 | Timmons et al. | 260/307 F |
| 3,953,432 | 4/1976 | Wehrmeister | 260/240 E |
| 3,979,405 | 9/1976 | Toth et al. | 260/307 F |

OTHER PUBLICATIONS

Toth et al.—C.A. 85, 21604v (1976).

*Primary Examiner*—Raymond V. Rush
*Attorney, Agent, or Firm*—Karl F. Ross

[57] ABSTRACT

2-phenoxy-, 2-phenylthio-, and 2-phenylamino-alkyl-2-oxazolines suitable for pharmaceutical use as hypolipemic and hypocholestric agents are disclosed.

1 Claim, No Drawings

2-PHENOXY AND 2-PHENYLTHIO AND 2-PHENYLAMINO-ALKYL-2-OXAZOLINES

This application is a continuation-in-part of Ser. No. 406,784 filed Oct. 16, 1973 now U.S. Pat. No. 3,979,405 issued Sept. 7, 1976.

This invention relates to a new 2-oxazoline derivatives, a process for the preparation thereof and pharmaceutical compositions containing the same.

In the prior art a number of 2-oxazoline derivatives are described. Some of these 2-oxazoline derivatives are substituted in position 2 by an alkyl, alkenyl, aralkyl, aralkenyl, aryl or cycloalkyl group while other compounds are 2-amino-2-oxazoline derivatives in which the nitrogen atom bears a substituent and are partly similar to the above groups (1) cf. Chemical Review, 71, 483; (1971); Angew. Chem. 84, 343; (1972). These known compounds possess fungicidal, antibacterial, central-nervous-system-regulating, anorexigenic, blood-pressure-decreasing, acetylcholine-esterase inhibiting and hypoglycemic properties.

The 2-(biphenyl-methyl)-2-oxazoline derivatives exhibit antiphlogistic activity (Belgian Patent No. 474,100), while the 5-(3,4-dihalogeno-phenoxy-methyl)-2-amino-oxazolines possess antimicrobial properties (U.S. Pat. No. 3,637,726).

According to the present invention there are provided new 2-oxazoline derivatives of the formula (I)

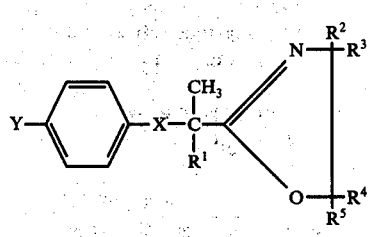

wherein
$R^1$ is hydrogen or an alkyl group having 1–4 carbon atoms;
$R^2$ and $R^3$ are hydrogen but where both $R^4$ and $R^5$ are hydrogen,
$R^2$ and $R^3$ are alkyl groups having 1–4 carbon atoms or hydroxymethyl groups;
$R^4$ and $R^5$ are hydrogen but where both $R^2$ and $R^3$ are hydrogen,
$R^4$ and $R^5$ are alkyl groups having 1–4 carbon atoms, amino groups, which can be mono- or disubstituted by alkyl groups having 1–4 carbon atoms, or are allyloxymethyl groups;
X is oxygen or sulphur or NH;
Y is a halogen atom or phenyl or halogen substituted phenyl.

The new compounds of the formula I differ from the known compounds both in their chemical structure 2-[aryl(oxy-, thio- or amino-)-alkyl]-2-oxazoline derivatives and their therapeutical utility. Contrary to the known compounds they exert hypolipemic and hypocholesteric effects.

Representatives of the compounds of the formula (I) are the following:

2-[(p-chlorophenoxy)-isopropyl]-4-methyl-4-hydroxymethyl-2-oxazoline;

2-[(p-chlorophenoxy)-isopropyl]-4-ethyl-4-hydroxymethyl-2-oxazoline;

2-[(p-chlorophenoxy)-isopropyl]-4,4-bis-hydroxymethyl-2-oxazoline;

2-{[4'(4''-chlorophenyl)-phenoxy]-isorpopyl}-4,4-bis-hydroxymethyl-2-oxazoline;

2-{[4'-(4''-chlorophenyl)-phenoxy]-isopropyl}-4-methyl-4-hydroxymethyl-2-oxazoline; and 2-[2-(p-chlorophenoxy)-butyl-2]-4-methyl-4-hydroxymethyl-2-oxazoline. A preferred compound is 2-{[4'-(4''-chlorophenyl)-phenoxy]-isopropyl}-4-ethyl-4-hydroxymethyl-2-oxazoline.

According to a further feature of the present invention there is provided a process for the preparation of compounds of the formula (I)

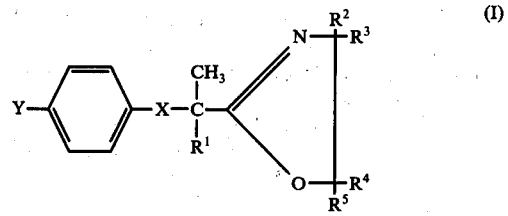

which comprises reacting a compound of the formula (II)

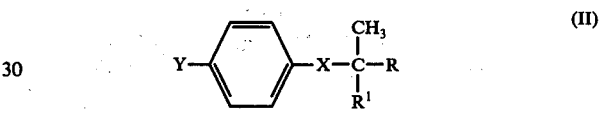

wherein R is a nitrile or carboxy group and $R^1$, X and Y are as described above with the proviso that if X stands for an NH group, R is a carboxy group, with a β-aminoalcohol of the formula (III)

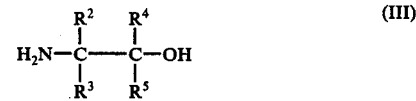

If a caboxylic acid of the formula (II) is used as the starting material, it is preferred to use the β-aminoalcohol of the formula (III) in a stoichiometric equivalent or up to an excess of 50%, preferably 10 to 25%, and to carry out the reaction in anhydrous xylene at the boiling point of the reaction mixture. The water formed in the reaction may be continuously removed from the reaction mixture as an azeotropic mixture of xylene and water by using a water-separating apparatus. On heating the reaction mixture to boiling for 8–12 hours, the desired product is obtained.

If a nitrile of the formula (III) is used as the starting material, the reaction is preferably accomplished in an anhydrous solvent or in the absence of a solvent. The reaction can be carried out in the presence of a catalyst and at a temperature of 100° to 180° C. As the solvent an excess (of 50 to 100%) of one of the starting materials (preferably amino alcohol) or an anhydrous alcohol (such as n-butanol or cyclohexanol) may be used. The catalyst is an alkali alcoholate (preferably sodium methylate or sodium ethylate) or a soluble zinc or cadmium salts (preferably cadmium acetate, zinc acetate or zinc chloride). The catalyst is used in an amount of 0.03–0.1 mole of catalyst/mole of reactant. In the course of the reaction gaseous ammonia is evolved and the end of the reaction its presence is indicated by the termination of the development of ammonia gas.

The starting materials of the formulae II and III are partially known.

The compounds of the formula (II) may be prepared by known methods see: Ber., 52, 89; (1929); Gazz. chim. ital., 36, 334; (1906); Arkiv Kemi, 7,437, 1954; J. Med. Chem. 12, 1001; (1969). The β-amino-alcohols of the formula (III) can also be prepared by known methods (German Patent No. 718,569, U.S. Pat. No. 2,413,153).

Of the nitriles used as starting material the 2-[4-(4'-chlorophenyl)-phenoxy]-2-methyl-propionitrile is a new compound which may be prepared by reacting the corresponding acid amide with phosphorous oxychloride at a temperature between 80° C. and 90° C.

In the process of the present invention the following starting materials are preferably used:

Carboxylic acids of the formula (II): α-(p-chlorophenoxy)-propionic acid;
2-(p-chlorophenoxy)-2-methyl-propionic acid;
2-(p-bromophenoxy)-2-methyl-propionic acid;
2-(p-chlorophenyl-thio)-2-methyl-propionic acid;
2-(p-chloroanilino)-2-methyl-propionic acid;
2-[4-(4'-chlorophenyl)-phenoxy]-2-methyl-propionic acid;

Nitriles of the formula (II): 2-(p-chlorophenoxy)-2-methyl-propionitrile;
2-(p-chlorophenoxy)-2-methyl-butyronitrile;
2-(p-chlorophenylthio)-2-methyl-propionitrile;
2-[4-(4'-chlorophenyl)-phenoxy]-2-methyl-propionitrile.

Amino-alcohols of the formula (III): ethanolamine;
1-amino-2-propanol;
2-amino-1-butanol;
2-amino-2-methyl-1-propanol;
2-amino-2-methyl-1,3-propane-diol;
2-amino-2-ethyl-1,3-propanediol;
2-amino-2-hydroxy-methyl-1,3-propane-diol;
1-amino-3-diethylamino-2-propanol;
3-allyloxy-2-oxypropyl-amine-1.

The new 2-oxazoline-derivatives of the formula (I) possess useful pharmacological activity and may be used as active cholesterol-level and lipid-level decreasing agents. Thus in a dose of 30–150 mg/kg they provide the same result as ethyl-2-(p-chlorophenoxy)-2-methyl-propionate (Atromid, a wellknown and generally used drug in the field of cholesterol reduction) when used in a dose of 300 mg/kg. The compounds of the formula (I) are not toxic and do not give any symptoms of toxicity even when administered in an oral dose of 1000 mg/kg. Thus the therapeutical index of the compounds of the present invention is significantly more favorable than that of Atromid.

The therapeutical acticity of the compounds of the present invention is demonstrated by Table I. The following test method was used: male rats weighing 180–200 g were treated for 10 days with 10, 30, 100 and 300 mg/kg, respectively, oral doses of the test compound. The animals were used in groups of 10 for each dose. As reference compound Atromid was used in an oral dose of 100 and 300 mg/kg. On the 11th day the animals were bled and the total cholesterol content [Zlatkis, A.; Zak, B.; Boyle, A. J.; Lab. clin. Med. 41, 486; (1953)], the triglyceride content [Van Handel, E.; Zilversmit, D. B.; J. Lab. clin. Med. 50, 152; (1957)] and the free fatty acid level [(Dole, V. P.; clin. Invest. 35, 150; (1956)] of the serum was determined. The change of body weight and liver weight of the animals and the cholesterol and triglyceride content of the liver after extraction was measured [Folch, J.; Lees, M.; Stanley, G. H.; J. biol. Chem. 266, 497; (1957)].

The results are demonstrated in Table I.

According to the present invention there are also provided pharmaceutical compositions comprising as active ingredient compounds of the formula (I) in admixture with suitable inert non-toxic, solid or liquid carriers. The compositions may be used in solid form (tablets, dragees) or in liquid form (solution, emulsion, suspension). The compositions may be prepared by known methods of the pharmaceutical industry. Usual carriers (e.g. talc, starch, magnesium stearate, calcium carbonate, etc.) may be used. The compositions may optionally comprise additives (e.g. wetting, disintegrating, emulsifying agents, etc.) and other biologically active compounds.

TABLE I

| Compound | Dose mg/kg Oral | % Change Of Body Weight | % Change Of Liver Weight | % Change Of Serum Cholesterol Content | % Change Of Serum Triglyceride Content | % Change Of Serum Free Fatty Acid Content | % Change Of Liver Cholesterol Content | % Change Of Liver Triglyceride Content |
|---|---|---|---|---|---|---|---|---|
| 2-[2'-(p-chlorophenoxy)-isopropyl]-4,4-bis-hydroxy-methyl-Δ²-oxazoline | 10 | +16.1 | − 5.14 | + 5.9 | −13.4 | +18.2 | +17.6 | + 6.9 |
| | 30 | +25.6 | − 6.50 | φ | + 3.8 | +13.6 | +12.8 | −4.3 |
| | 100 | +19.3 | + 9.50 | −12.3 | −12.6 | −24.3 | +12.7 | −10.1 |
| | 300 | +11.7 | +31.70 | −38.5 | −44.5 | φ | + 9.7 | −18.8 |
| control | | +23.5 | — | — | — | — | — | — |
| control | | +32.1 | — | — | — | — | — | — |
| 2-[2'-(p-chlorophenoxy)-isopropyl]-4-ethyl-4-hydroxy-methyl-Δ²-oxazoline | 10 | +20.6 | φ | − 0.4 | −44.8 | −19.9 | φ | −17.3 |
| | 30 | +26.3 | − 1.4 | −10.7 | −37.8 | −20.0 | + 0.7 | −33.2 |
| | 100 | +22.5 | + 7.9 | −31.3 | −41.3 | + 9.9 | + 8.4 | −27.5 |
| | 300 | +23.9 | +34.3 | −38.1 | −59.1 | − 9.9 | +8.7 | −54.2 |
| control | | +27.0 | — | — | — | — | — | — |
| 2-[2'-(p-chlorophenoxy)-isopropyl]-4-methyl-4-hydroxy-methyl-Δ²-oxazoline | 10 | +22.2 | + 2.0 | − 4.8 | + 7.8 | +10.1 | +16.3 | +12.5 |
| | 30 | +25.6 | + 8.0 | − 1.6 | − 7.1 | +16.9 | − 5.8 | −16.7 |
| | 100 | +26.9 | +32.8 | −23.3 | −29.0 | −11.0 | − 9.4 | − 5.1 |
| | 300 | +52.8 | +24.5 | −29.0 | −34.9 | + 3.3 | − 4.6 | +10.3 |
| Atromid-S control | | +20.7 | — | — | — | — | — | — |
| Atromid-S | 100 | +18.8 | +21.6 | − 9.7 | −37.4 | − 6.3 | − 5.1 | −10.7 |
| | 300 | +12.7 | +49.6 | −17.4 | −37.4 | −31.9 | − 3.8 | −31.9 |

The daily doses may vary within a wide range and depend on the condition of the patient and the details of the particular case. It is generally preferred to administer the compounds of the formula (I) in a daily amount of from about 300 mg to about 1.5 g.

A further advantage of the compounds of the formula (I) is their excellent absorption. It is noteworthy that the compounds of the present invention are generally crystalline substances which may be put on the market as tablets or dragees, i.e. in simple dosage unit forms, contrary to the oily Atromid which can be formulated only as pearl capsules.

Further details of the present invention are to be found in the Examples without limiting the scope of our invention to the Examples.

EXAMPLE I

2-[(p-chlorophenoxy)-isopropyl]-4-ethyl-4-hydroxymethyl-2-oxazoline 19.57 g (0.1 moles) of 2-(p-chlorophenoxy)-2-methyl-propionitrile are reacted under stirring for 7 hours with 17.88 g (0.15 moles) of 2-amino-2-ethyl-1,3-propane-diol in the presence of 0.41 g (0.0075 moles) of sodium-methylate catalyst at a temperature between 140°–150° C. The reaction starts within a few minutes by an intensive development of ammonia gas at this temperature. The end of the reaction is indicated by the cessation of the gas development. After cooling to room temperature the grey-brown colored oil is dissolved in 200 ml of chloroform. The chloroform solution is washed with water to neutral reaction, the organic phase is dried on anhydrous magnesium sulphate and the chloroform is distilled off. The remaining oil (26.7 g) is admixed with 100 ml of petroleum ether and the precipitated crystals are filtered out and dried. The raw product 2-[(p-chlorophenoxy)-isopropyl]-4-ethyl-4-hydroxy-methyl-2-oxazoline obtained (22 g) is dissolved in 30 ml of benzene and after the addition of 80 ml of petroleum ether the mixture is cooled to −10° C. and precipitated white crystals are filtered. 19.35 g of the product are obtained. M.p.: 94°–95° C.

EXAMPLE II

2-{[4-(4′-chlorophenyl)-phenoxy]-isopropyl}-4,4-bis-hydroxymethyl-2-oxazoline 27.17 g (0.1 moles) of 2-[4-(4′chlorophenyl)-phenoxy]-2-methyl-propionitrile are reacted under stirring for 10 hours with 18.17 g (0.15 moles) of 2-amino-2-hydroxy-methyl-1,3-propane-diol in the presence of 0.41 g (0.0075 moles) of sodium-methylate caalyst at a temperature of 150°–160° C. The reaction takes place under an intensive development of ammonia gas. The reaction finished, the reaction mixture is cooled to room temperature; the obtained green-brown colored resin-like product is dissolved in 120 ml of hot ethanol, 40 ml of water are added to the solution, whereupon it is decolored with charcoal at room temperature. 250 ml of water are added to the decolorized solution which is cooled to +5° C. and the precipitated product 2-{[4-(4′-chlorophenyl)-phenoxy]-isopropyl}-4,4-bis-hydroxymethyl-2-oxazoline is filtered and dried. The dry product (32 g), m.p.: 138°–143° C. is purified by recrystallization from ethylacetate. The recrystallized product 22.57 g, yield 60%, has a m.p. of 151.5°–152° C.

Preparation of the starting material, the 2-[4-(4′-chlorophenyl)-phenoxy]-2-methyl propionitrile and 28.98 g (0.1 moles) of 2-[4-(4′-chlorophenyl)-phenoxy]-2-methyl-propionamide are reacted under stirring for 3 hours with 25 ml (0.27 moles) of phosphorous oxychloride at a temperature of 80°–90° C. The reaction takes place under an intensive development of hydrochloric acid gas. When the reaction is finished, the mixture is cooled to room temperature and is poured carefully under continual stirring into 200 g of chopped ice. The ice melted, the precipitated brown-colored crystalline product is filtered and washed with water to neutral reaction (free from acid). The well-filtered product is dissolved in 150 ml of anhydrous alcohol, the solution is decolorized at 60° C. with charcoal and filtered. 100 ml water are added to the filtrate, then it is cooled in ice water and the precipitated beige-colored crystals are filtered off and dried. 14.93 g of the product are obtained (yield 55%), m.p.: 76°–77° C.

EXAMPLE III

2-[(p-chlorophenylthio)-isopropyl]-4,4-bis-hydroxymethyl-2-oxazoline 21.17 g (0.1 moles) of 2-(p-chlorophenylthio)-2-methyl-propionitrile are reacted under stirring for 8 hours with 18.17 g (0.15 moles) of 2-amino-2-hydroxy-methyl-1,3-propanediol in the presence of 0.54 g (0.01 moles) of sodium-methylate catalyst at a temperature of 170°–180° C. When the reaction is finished, the mixture is cooled to 25° C. and dissolved in 200 ml of chloroform. The insoluble part is filtered off and the chloroform solution washed with water to neutral reaction. The solution is dried over anhydrous magnesium sulphate and evaporated to dryness. The residue was 25.6 g, m.p.: 85°–90° C. After recrystallization from a benzene-petroleumether mixture 15.8 g of the product 2-[(p-chlorophenylthio)-isopropyl]-4,4-bis-hydroxymethyl-2-oxazoline are obtained (yield 50%), m.p.: 110°–112° C.

EXAMPLE IV

2-[(p-chlorophenoxy)-isopropyl]-4,4-dimethyl-2-oxazoline 19.57 g (0.1 moles) of 2-(p-chlorophenoxy)-2-methyl-propionitrile are reacted under stirring for 34 hours with 17.83 g (0.2 moles) of 2-amino-2-methyl-1-propanol in the presence of 0.66 g (0.003 moles) of zinc-acetate catalyst at a temperature of 140°–150° C. The reaction takes place under an intensive development of ammonia gas. When the gas development is finished, the mixture is cooled, dissolved in 300 ml of chloroform and the solution washed with water to neutral reaction. After drying the solution over anhydrous magnesium sulphate, it is evaporated to dryness. The green-yellow colored oil (26.5 g) is subjected to fractional distillation in vacuo. The main fraction is a product 2-[(p-chlorophenoxy)-isopropyl]-4,4-dimethyl-2-oxazoline of 23.6 g (yield 88%), m.p.: 98°–100° C./0.02 mmHg. The distilled product crystallizes after standing for 48 hours, m.p.: 59°–61° C.

EXAMPLE V

The process is as described in Example IV, with the only difference that, instead of zinc acetate, in the same molecular proportion, zinc-chloride catalyst is used. The weight of the product obtained equals 23 g (yield 86%).

EXAMPLE VI

The process is as described in Example IV, with the only difference that, instead of zinc acetate, in the same molecular proportion, cadmium acetate is used. The weight of the product obtained equals 23.2 g (yield 87%).

EXAMPLE VII

The process is as described in Example I, with the only difference that, instead of sodium methylate, in the same molecular proportion, sodium-ethylate catalyst is used. The weight of the product obtained equals 19 g (yield 64%).

EXAMPLE VIII

The process is as described in Example II, with the only difference that, instead of the aminoalcohol, an excess of 10 ml of n-butanol is used as solvent. The weight of the product obtained equals 22.18 g (yield 59%).

EXAMPLE IX

The process is as described in Example III, with the only difference that, instead of the aminoalcohol, an excess of 10 ml of cyclohexanol is used as solvent. The weight of the product obtained equals 15.15 g (yield 48%).

EXAMPLES X–XVII

The process is analogous to those in Examples I–VI. The data of the compounds prepared are indicated in Table II.

EXAMPLE XIX

2-{[4′(4″-chlorophenyl)-phenoxy]-isopropyl}-4-hydroxy-methyl-4-methyl-2-oxazoline 29.07 g (0.1 moles) of 2-[4-(4′-chlorophenyl)-phenoxy]-2-methyl-propionic acid and 13.15 g (0.125 moles) of 2-amino-2-methyl-1,3-propane diol dissolved in 1400 ml of anhydrous xylene are boiled for 11 hours in an apparatus provided with a water-separating column. The accumulated water-xylene mixture is occasionally removed from the column. When no more water is evolved from the system the boiling is stopped. The xylene is distilled off in vacuo and the partly crystalline partly oily residue is admixed with 300 ml. of ether. After standing for some hours the crystals are filtered off and the ether filtrate is decolorized with active carbon (charcoal) and then evaporated to dryness. The residue is admixed with a cyclohexane-ether mixture (4:1) and after 2 days the precipitated crystals are filtered out. The dried crude product of 17.6 g has a m.p. of 123°–127° C. It is recrystallized from an alcohol-

TABLE II

| Example | $R^1$ | $R^2$ | $R^3$ | $R^4$ | $R^5$ | X | Y | Yield (%) Catalyst A | B | C | D | M.P. ° C B.P. ° C/HG MM |
|---|---|---|---|---|---|---|---|---|---|---|---|---|
| 10. | —CH$_3$ | H | H | H | H | O | Cl | 40 | 65 | 67 | 70 | 106/0.1 |
| 11. | —CH$_3$ | —C$_2$H$_5$ | H | H | H | O | Cl | 45 | 67 | 69 | 73 | 130/0.3 |
| 12. | —CH$_3$ | —CH$_3$ | —CH$_2$OH | H | H | O | Cl | 65 | 75 | 86 | 88 | 71–72 138/0.15 |
| 13. | —CH$_3$ | —CH$_2$OH | —CH$_2$OH | H | H | O | Cl | 75 | 73 | 88 | 87 | 141–142 |
| 14. | —C$_2$H$_5$ | —CH$_3$ | —CH$_2$OH | H | H | O | Cl | 75 | 76 | 84 | 87 | 135/0.05 |
| 15. | —CH$_3$ | H | H | —CH$_3$ | H | O | Cl | 43 | 62 | 64 | 71 | 126/0.4 |
| 16. | —CH$_3$ | H | H | —CH$_2$N(C$_2$H$_5$)2 | H | O | Cl | 70 | 75 | 76 | 81 | 140/0.1 |
| 17. | —CH$_3$ | H | H | —CH$_2$OCH$_2$CH=CH$_2$ | H | O | Cl | 64 | — | — | — | 148/0.2 |

A = NaOCH$_3$;
B = ZnCl$_2$;
C = Zn(CH$_3$COO)$_2$2H$_2$O;
D = Cd(CH$_3$COO)$_2$2H$_2$O.

EXAMPLE XVIII

2-[(p-chlorophenoxy)-isopropyl]-4,4-bis-hydroxy-methyl-2-oxazoline water mixture (4:3). The end product 2-{[4′(4″-chlorophenyl)-phenoxy]-isopropyl}-4-hydroxy-methyl-4-methyl-2-oxazoline obtained (10.8 g, yield 30%) has a m.p. of 130°–131° C.

TABLE III

| Example | $R^1$ | $R^2$ | $R^3$ | $R^4$ | $R^5$ | X | Y | Yield % | M.P. ° C B.P. ° C/MM HG |
|---|---|---|---|---|---|---|---|---|---|
| 20. | CH$_3$— | —CH$_2$OH | —CH$_2$OH | H | H | —NH— | Cl | 38 | 116–118 |
| 21. | CH$_3$— | CH$_3$— | —CH$_2$OH | H | H | O | C$_6$H$_5$ | 31 | 101–102 |
| 22. | CH$_3$— | —CH$_2$OH | —CH$_2$OH | H | H | O | Br | 39 | 130–131 |
| 23. | CH$_3$— | CH$_3$— | —CH$_2$OH | H | H | S | Cl | 42 | 64–66 |
| 24. | CH$_3$— | C$_2$H$_5$— | —CH$_2$OH | H | H | S | Cl | 41 | 150–160/1.0 |
| 25. | H | —CH$_2$OH | —CH$_2$OH | H | H | O | Cl | 40 | 148–150 |

21.45 g (0.1 moles) of 2-(p-chlorophenoxy)-2-methyl-propionic acid and 15.14 g (0.125 moles) of 2-amino-2-hydroxy-methyl-1,3-propane-diol are boiled for 12 hours in 900 ml. anhydrous xylol in an appratus provided with a water-separating column. The water formed during the course of the reaction is accumulated as an azeotropic mixture in the water-separating column from where it is removed from time to time. When no more water is evolved from the system the boiling is stopped. The hot xylene solution is discharged from the insoluble part. After cooling the white crystals precipitated from the xylene solution are filtered off and washed with benzene. After drying, the crude product 2-[(p-chlorophenoxy)-isopropyl]-4,4-bis-hydroxy-methyl-2-oxazoline obtained (21.8 g, m.p.: 133°–135° C.) is recrystallized from 70% aqueous ethanol. The pure product (12 g, yield 40%) has a m.p. of 141.5°–142.5° C.

EXAMPLES XX–XXV

The process is analogous to that described in EXAMPLE XVIII. The data of the compounds prepared are indicated in TABLE III.

EXAMPLE XXVI

The process of EXAMPLE XIX is carried out except that 0.125 moles of 2-amino-2-ethyl-1,3-propane-diol is used as the aminoalcohol. The product in a yield of about 30% is 2-{[4′-(4″-chlorophenyl)-phenoxy]-isopropyl}-4-ethyl-4-hydroxy-methyl-oxazoline.

EXAMPLE XXVII

As test animals male rats weighing 180–200 g were used. The test compounds were administered in oral doses of 3–10–30–100 mg/kg and 30–100 mg/kg respectively. The treatment was carried out during 10 days.

After this period the animals were bled in ether narcosis and the total cholesterol level [Zlatkis, A.; Zak, B.; Boyle, A. J.: *J. Lab. clin. Med.* 41, 486; (1953)], the triglyceride level [Van Handel, E.; Zilversmit, D. B.: *J. Lab. clin. Med.* 50, 152; (1957)] and free fatty acid level [Doyle, V. P.: *J. clinInvest.* 35, 150; (1956)] of the serum and in some instances the cholesterol and triglyceride content of the liver were determined. Tissue extract was carried out by the method of Folch, J.; Less, M.; Sloane Stanley, G. H.: *J. Biol. Chem.* 26, 497; (1957)].

As control ethyl-α(p-chlorophenoxy)-isobutyrate was used in oral doses of 100 and 300 mg/kg respectively.

Detailed evaluation of the comparative tests is as follows:

1st Compound: The minimal serum cholesterol decreasing dose is 3 mg/kg but it decreases the triglyceride level of serum already in a dose of 1 mg/kg p.o. (orally) to a considerable extent. In higher doses it decreases the triglyceride content of liver. It is about 30–100 times more active than the control.

2nd Compound: The minimal serum cholesterol and triglyceride decreasing dose is 30 mg/kg. It is about 3–10 times more active than the control.

3rd Compound: Minimal serum cholesterol and triglyceride decreasing dose is 3 mg/kg. The compound is about 30 times more active than the control.

4th Compound: The minimal serum cholesterol and triglyceride decreasing dose is 30 mg/kg. The compound is about 3–10 times more active than the control.

5th Compound: This compound does not decrease the cholesterol level of serum. From the point of view of the serum triglyceride level decreasing effect it is however about 3 times more active than the control.

See Table IV.

TABLE IV

| Compound | Dose Mg/kg Oral | #Rats Examined | % Change Of Body Weight | % Change Of Liver Weight | % Change Of Serum Cholesterol Content | % Change Of Serum Triglyceride Content | % Change Of Serum Free Fatty Acid Content | % Change Of Liver Cholesterol Content | % Change Of Liver Triglyceride Content |
|---|---|---|---|---|---|---|---|---|---|
| Control | — | 20 | +37.2 | — | — | — | — | — | — |
| 2-{[4'-(4''-chlorophenyl)-phenoxyl]-isopropyl}-4-ethyl-4-hydroxy-methyl-2-oxazoline (first) | 1 | 10 | +33.9 | + 4.8 | − 9.7 | −39.4 | φ | −10.9 | φ |
| | 3 | 20 | +27.6 | + 6.4 | −25.6 | −51.4 | + 7.1 | +15.8 | +29.0 |
| | 10 | 20 | +33.8 | +30.5 | −28.3 | −62.1 | + 28.0 | + 2.7 | +20.8 |
| | 30 | 20 | +30.6 | +57.8 | −32.0 | −61.6 | + 71.5 | − 6.1 | −10.8 |
| | 100 | 10 | +32.1 | +70.0 | −19.1 | −52.0 | +101.7 | − 5.3 | −41.6 |
| Control | — | 8 | +50.0 | — | — | — | — | — | — |
| 2-[(p-bromo-phenoxy)-isopropyl]-4-ethyl-4-hydroxy-methyl-2-oxazoline (second) | 30 | 6 | +44.5 | + 6.7 | −19.1 | −25.6 | − 14.6 | — | — |
| | 100 | 6 | +44.0 | +13.4 | −22.2 | −35.9 | − 1.3 | — | — |
| Control | — | 10 | +35.2 | — | — | — | — | — | — |
| 2-{[4'-(4''-chlorophenyl)-phenoxy]-isopropyl}-4-methyl-4-hydroxy-methyl-2-oxazoline (third) | 3 | 10 | +32.5 | +19.5 | −28.0 | −27.5 | − 1.7 | + 3.6 | +16.6 |
| | 10 | 10 | +32.6 | +56.1 | −21.0 | +35.1 | + 12.0 | + 5.6 | − 8.3 |
| | 30 | 10 | +30.9 | +85.3 | −31.7 | −10.0 | + 33.3 | −13.5 | −25.0 |
| | 100 | 10 | +17.1 | +96.8 | −24.6 | −27.7 | + 72.0 | +12.9 | −38.0 |
| Control | — | 8 | +33.6 | — | — | — | — | — | — |
| 2-[(4'-phenyl-phenoxy)-isopropyl]-4-ethyl-4-hydroxy-methyl-2-oxazoline (fourth) | 30 | 6 | +34.0 | +18.0 | −13.4 | −27.1 | + 32.4 | — | — |
| | 100 | 6 | +39.1 | +38.5 | −20.1 | −45.7 | + 44.4 | — | — |
| Control | — | 8 | +25.6 | — | — | — | — | — | — |
| 2-[(p-chlorophenylthio)-isopropyl]-4,4-bis-hydroxy-methyl-2-oxazoline (fifth) | 30 | 6 | +32.1 | − 4.7 | − 8.2 | −22.2 | + 5.3 | — | — |
| | 100 | 6 | +27.3 | − 3.1 | −12.0 | −59.2 | + 3.2 | — | — |

We claim:
1. 2-[4'-(4''-Chlorophenyl)-phenoxy]-isopropyl-4-ethyl-4-hydroxy-methyl-oxazoline.

* * * * *